United States Patent
Armstrong (10) Patent No.: US 8,428,731 B2
(45) Date of Patent: Apr. 23, 2013

(54) SEQUENCED THERAPY PROTOCOLS FOR AN IMPLANTABLE MEDICAL DEVICE

(75) Inventor: Randolph Armstrong, Houston, TX (US)

(73) Assignee: Cyberonics, Inc., Houston, TX (US)

(*) Notice: Subject to any disclaimer, the term of this patent is extended or adjusted under 35 U.S.C. 154(b) by 2227 days.

(21) Appl. No.: 11/260,836

(22) Filed: Oct. 27, 2005

(65) Prior Publication Data

US 2007/0100391 A1    May 3, 2007

(51) Int. Cl.
*A61N 1/00* (2006.01)

(52) U.S. Cl.
USPC .................................. 607/45; 607/2

(58) Field of Classification Search .............. 607/2, 45
See application file for complete search history.

(56) References Cited

U.S. PATENT DOCUMENTS

| | | |
|---|---|---|
| 3,760,812 A | 9/1973 | Timm et al. |
| 4,305,402 A | 12/1981 | Katims |
| 4,338,945 A | 7/1982 | Kosugi et al. |
| 4,424,812 A | 1/1984 | Lesnick |
| 4,431,000 A | 2/1984 | Butler et al. |
| 4,459,989 A | 7/1984 | Borkan |
| 4,503,863 A | 3/1985 | Katims |
| 4,573,481 A | 3/1986 | Bullara |
| 4,590,946 A | 5/1986 | Loeb |
| 4,608,985 A | 9/1986 | Crish et al. |
| 4,612,934 A | 9/1986 | Borkan |
| 4,628,942 A | 12/1986 | Sweeney et al. |
| 4,649,936 A | 3/1987 | Ungar et al. |
| 4,702,254 A | 10/1987 | Zabara |
| 4,867,164 A | 9/1989 | Zabara |
| 4,920,979 A | 5/1990 | Bullara |
| 4,949,721 A | 8/1990 | Toriu et al. |
| 5,025,807 A | 6/1991 | Zabara |
| 5,154,172 A | 10/1992 | Terry, Jr. et al. |
| 5,188,104 A | 2/1993 | Wernicke et al. |
| 5,205,285 A | 4/1993 | Baker, Jr. |
| 5,215,086 A | 6/1993 | Terry, Jr. et al. |
| 5,222,494 A | 6/1993 | Baker, Jr. |
| 5,231,988 A | 8/1993 | Wernicke et al. |
| 5,263,480 A | 11/1993 | Wernicke et al. |
| 5,269,303 A | 12/1993 | Wernicke et al. |
| 5,299,569 A | 4/1994 | Wernicke et al. |
| 5,330,507 A | 7/1994 | Schwartz |

(Continued)

FOREIGN PATENT DOCUMENTS

| | | |
|---|---|---|
| EP | 1070518 | 5/1984 |
| WO | 2004036377 A2 | 4/2004 |
| WO | 2004112894 A1 | 3/2005 |
| WO | 2005028026 A1 | 3/2005 |

OTHER PUBLICATIONS

Bachman, D.S, et al., "Effects of Vagal Volleys and Serotonin on Units of Cingulate Cortex in Monkeys," Brain Research, 130, (1977), pp. 253-269.

Boon, Paul et al., "Programmed and Magnet-Induced Vagus Nerve Stimulation for Refractory Epilepsy," Journal of Clinical Neurophysiology, vol. 18, No. 5, 2001, pp. 402-407.

(Continued)

*Primary Examiner* — Niketa Patel
*Assistant Examiner* — Alyssa M Alter
(74) *Attorney, Agent, or Firm* — Cyberonics, Inc.

(57) ABSTRACT

In one embodiment of the invention, a method comprises (a) implementing a first therapy in an implantable medical device (IMD) from a programmed sequence of therapies for a first time period, (b) implementing a second therapy from the sequence in the IMD for a second time period following the first time period, and repeating (a) and (b).

23 Claims, 4 Drawing Sheets

U.S. PATENT DOCUMENTS

| | | |
|---|---|---|
| 5,330,515 A | 7/1994 | Rutecki et al. |
| 5,334,221 A | 8/1994 | Bardy |
| 5,354,320 A | 10/1994 | Schaldach et al. |
| 5,411,531 A | 5/1995 | Hill et al. |
| 5,411,540 A | 5/1995 | Edell et al. |
| 5,423,872 A | 6/1995 | Cigaina |
| 5,507,784 A | 4/1996 | Hill et al. |
| 5,522,865 A | 6/1996 | Schulman et al. |
| 5,540,730 A | 7/1996 | Terry, Jr. et al. |
| 5,540,734 A | 7/1996 | Zabara |
| 5,571,150 A | 11/1996 | Wernicke et al. |
| 5,601,617 A | 2/1997 | Loeb et al. |
| 5,645,570 A | 7/1997 | Corbucci |
| 5,651,378 A | 7/1997 | Matheny et al. |
| 5,658,318 A | 8/1997 | Stroetmann et al. |
| 5,690,681 A | 11/1997 | Geddes et al. |
| 5,690,688 A | 11/1997 | Noren et al. |
| 5,700,282 A | 12/1997 | Zabara |
| 5,702,429 A | 12/1997 | King |
| 5,707,400 A | 1/1998 | Terry, Jr. et al. |
| 5,755,750 A | 5/1998 | Petruska et al. |
| 5,792,212 A | 8/1998 | Weijand |
| 5,814,092 A | 9/1998 | King |
| 5,836,994 A | 11/1998 | Bourgeois |
| 5,861,014 A | 1/1999 | Familoni |
| 5,916,239 A | 6/1999 | Geddes et al. |
| 5,928,272 A | 7/1999 | Adkins et al. |
| 6,002,966 A | 12/1999 | Loeb et al. |
| 6,101,412 A | 8/2000 | Duhaylongsod |
| 6,104,956 A | 8/2000 | Naritoku et al. |
| 6,132,361 A | 10/2000 | Epstein et al. |
| 6,141,590 A | 10/2000 | Renirie et al. |
| 6,175,764 B1 | 1/2001 | Loeb et al. |
| 6,219,580 B1 | 4/2001 | Faltys et al. |
| 6,266,564 B1 | 7/2001 | Hill et al. |
| 6,269,270 B1 | 7/2001 | Boveja |
| 6,295,472 B1 | 9/2001 | Rubinstein et al. |
| 6,308,102 B1 | 10/2001 | Sieracki et al. |
| 6,339,725 B1 | 1/2002 | Naritoku et al. |
| 6,341,236 B1 | 1/2002 | Osorio et al. |
| 6,356,788 B2 | 3/2002 | Boveja |
| 6,366,813 B1 | 4/2002 | DiLorenzo |
| 6,366,814 B1 | 4/2002 | Boveja et al. |
| 6,374,140 B1 | 4/2002 | Rise |
| 6,381,496 B1 | 4/2002 | Meadows et al. |
| 6,381,499 B1 | 4/2002 | Taylor et al. |
| 6,418,344 B1 | 7/2002 | Rezai et al. |
| 6,425,852 B1 | 7/2002 | Epstein et al. |
| 6,449,512 B1 | 9/2002 | Boveja et al. |
| 6,463,328 B1 | 10/2002 | John |
| 6,473,644 B1 | 10/2002 | Terry, Jr. et al. |
| 6,480,743 B1 | 11/2002 | Kirpatrick et al. |
| 6,487,446 B1 | 11/2002 | Hill et al. |
| 6,505,074 B2 | 1/2003 | Boveja et al. |
| 6,522,928 B2 | 2/2003 | Whitehurst et al. |
| 6,532,388 B1 | 3/2003 | Hill et al. |
| 6,549,804 B1 | 4/2003 | Osorio et al. |
| 6,556,868 B2 | 4/2003 | Naritoku et al. |
| 6,564,102 B1 | 5/2003 | Boveja |
| 6,579,280 B1 | 6/2003 | Kovach et al. |
| 6,587,719 B1 | 7/2003 | Barrett et al. |
| 6,587,724 B2 | 7/2003 | Mann |
| 6,587,727 B2 | 7/2003 | Osorio et al. |
| 6,591,138 B1 | 7/2003 | Fischell et al. |
| 6,600,953 B2 | 7/2003 | Flesler et al. |
| 6,609,025 B2 | 8/2003 | Barrett et al. |
| 6,609,030 B1 | 8/2003 | Rezai et al. |
| 6,611,715 B1 | 8/2003 | Boveja |
| 6,615,081 B1 | 9/2003 | Boveja |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,628,987 B1 | 9/2003 | Hill et al. |
| 6,656,960 B2 | 12/2003 | Puskas |
| 6,668,191 B1 | 12/2003 | Boveja |
| 6,671,555 B2 | 12/2003 | Gielen et al. |
| 6,671,556 B2 | 12/2003 | Osorio et al. |
| 6,684,104 B2 | 1/2004 | Gordon et al. |
| 6,684,105 B2 | 1/2004 | Cohen et al. |
| 6,690,973 B2 | 2/2004 | Hill et al. |
| 6,690,974 B2 | 2/2004 | Archer et al. |
| 6,708,064 B2 | 3/2004 | Rezai |
| 6,731,979 B2 | 5/2004 | MacDonald |
| 6,731,986 B2 | 5/2004 | Mann |
| 6,754,536 B2 | 6/2004 | Swoyer et al. |
| 6,760,626 B1 | 7/2004 | Boveja |
| 6,764,498 B2 | 7/2004 | Mische |
| 6,768,969 B1 | 7/2004 | Nikitin et al. |
| 6,775,573 B2 | 8/2004 | Schuler et al. |
| 6,819,956 B2 | 11/2004 | DiLorenzo |
| 6,826,428 B1 | 11/2004 | Chen et al. |
| 6,832,114 B1 | 12/2004 | Whitehurst et al. |
| 6,853,862 B1 | 2/2005 | Marchal et al. |
| 6,885,888 B2 | 4/2005 | Rezai |
| 6,895,278 B1 | 5/2005 | Gordon |
| 6,920,357 B2 | 7/2005 | Osorio et al. |
| 6,944,501 B1 | 9/2005 | Pless |
| 6,961,618 B2 | 11/2005 | Osorio et al. |
| 7,050,856 B2 | 5/2006 | Stypulkowski |
| 7,054,686 B2 | 5/2006 | MacDonald |
| 2002/0099417 A1 | 7/2002 | Naritoku et al. |
| 2003/0236558 A1 | 12/2003 | Whitehurst et al. |
| 2004/0172094 A1 | 9/2004 | Cohen et al. |
| 2004/0210270 A1 | 10/2004 | Erickson |
| 2004/0210274 A1 | 10/2004 | Bauhahn et al. |
| 2004/0249416 A1 | 12/2004 | Yun et al. |
| 2005/0004621 A1 | 1/2005 | Boveja et al. |
| 2005/0060007 A1 | 3/2005 | Goetz |
| 2005/0060008 A1 | 3/2005 | Goetz |
| 2005/0060009 A1 | 3/2005 | Goetz |
| 2005/0060010 A1 | 3/2005 | Goetz |
| 2005/0065562 A1 | 3/2005 | Rezai |
| 2005/0065573 A1 | 3/2005 | Rezai |
| 2005/0065575 A1 | 3/2005 | Dobak |
| 2005/0075691 A1 | 4/2005 | Phillips et al. |
| 2005/0119703 A1 | 6/2005 | DiLorenzo |
| 2005/0131485 A1 | 6/2005 | Knudson et al. |
| 2005/0131506 A1 | 6/2005 | Rezai et al. |
| 2005/0154425 A1 | 7/2005 | Boveja et al. |
| 2005/0192644 A1 | 9/2005 | Boveja et al. |
| 2005/0283200 A1 | 12/2005 | Rezai et al. |
| 2006/0009815 A1 | 1/2006 | Boveja |
| 2006/0079936 A1 | 4/2006 | Boveja |
| 2006/0095081 A1 | 5/2006 | Zhou et al. |

OTHER PUBLICATIONS

DeGiorgio, Christopher M. et al., "Vagus Nerve Stimulation: Analysis of Device Parameters in 154 Patients During the Long-Term XE5 Study," Epilepsia, vol. 42, No. 8, 2001, pp. 1017-1020.

Fanselow, Erika E. et al., "Reduction of Pentylenetetrazole-Induced Seizure Activity in Awake Rats by Seizure-Triggered Trigeminal Nerve Stimulation," The Journal of Neuroscience, vol. 20, No. 21, Nov. 1, 2000, pp. 8160-8168.

Hallowitz, R.A., et al., "Effects of Vagal Volleys on Units of Intralaminar and Juxtalaminar Thalamic Nuclei in Monkeys," Brain Research, 130, (1977), pp. 271-286.

Harry, Jason D. et al., "Balancing Act," IEEE Spectrum, Apr. 2005, pp. 37-41.

Henry, Thomas R. et al., "Brain Blood Flow Alterations Induced by Therapeutic Vagus Nerve Stimulation in Partial Epilepsy: I. Acute Effects at High and Low Levels of Stimulation," Epilepsia, vol. 39, No. 9, 1998, pp. 983-990.

Lockard, J.S., et al., "Feasibility and Safety of Vagal Stimulation in Monkey Model," Epilepsia, 31, (Suppl.2), (1990), pp. S20-S26.

McClintock, Peter "Can Noise Actually Boost Brain Power?," Physics World, Physics in Action, Jul. 2002, pp. 20-21.

Mori, Toshio et al., "Noise-Induced Entrainment and Stochastic Resonance in Human Brain Waves," Physical Review Letters, vol. 88, No. 21, May 27, 2002, pp. 218101-1 to 218101-4.

Schacter, Steven C., et al., "Vagus Nerve Stimulation," Epilepsia, vol. 39, No. 7, 1998, pp. 677-686.

Terry, R.S., et al., "The Implantable Neurocybernetic Prosthesis System," Pacing and Clinical Electrophysiology, vol. 14, No. 1, (Jan. 1991), pp. 86-93.

SEQUENCED THERAPY PROTOCOLS FOR AN IMPLANTABLE MEDICAL DEVICE

BACKGROUND

1. Technical Field

The disclosed subject matter relates generally to implantable medical devices and more particularly to implantable medical devices that have multiple sequenced therapy protocols.

2. Background Information

Implantable medical devices typically operate according to a desired therapy. A vagus nerve stimulator (VNS), for example, electrically stimulates the patient's vagus nerve in accordance with a therapy that is characterized by such variables as pulse width, pulse amplitude, on time, off time, etc. A physician typically programs settings (pulse width, etc.) in the patient's medical device for a suitable therapy and the settings remain fixed until a physician opts to change the settings.

In at least some situations, however, it is desirable to change the settings. For example, a physician may want to have the patient's brain imaged (e.g., using fMRI or other imaging techniques) while the patient's implanted device is sequenced through multiple sets of settings (i.e., therapies) to determine an optimal therapy. Changing the settings during such imaging unfortunately requires repeated and time-consuming use of specialized programming equipment. By way of a further example, shortly following implantation it may be desired to initialize a setting to a therapeutically relatively low value and change (e.g., increase) that setting until an optimal value is reached for that particular patient. Current magnitude, for example, could be initialized to a relatively low value of current and then ramped up until an optimal patient-specific current magnitude is determined. Each change to a setting requires the patient to visit the physician, which naturally is time-consuming and burdensome.

BRIEF SUMMARY

Various apparatus and method embodiments of the invention are described herein. For example, in one embodiment of the invention, a method is implemented in an implantable medical device (IMD) that comprises a sequence of a plurality of pre-programmed therapies. The preferred method comprises (a) implementing a first therapy from the sequence in the IMD for a first time period and (b) implementing a predetermined second therapy from the sequence in the IMD for a second time period following the first time period. The method also comprises repeating (a) and (b).

In another embodiment, a method comprises implementing a first therapy in an IMD and causing the IMD to sequence through a plurality of therapies. After sequencing through the plurality of therapies, implementing and continuing the first therapy in the IMD and not automatically repeating said sequence.

In yet another embodiment, an implantable medical device comprises a pulse generator that provides an electrical pulse signal to stimulate a patient's tissue, and a controller coupled to the pulse generator. The controller causes a plurality of therapies to be implemented by said pulse generator in a repeating sequence.

An additional embodiment comprises an implantable medical device. The IMD comprises an electrical signal generator that provides an electrical pulse signal to stimulate a patient's tissue and a controller coupled to the pulse generator. The controller causes a first therapy implemented by the pulse generator to be interrupted, a plurality of therapies to then be implemented in sequence by the pulse generator, and the first therapy to again be implemented.

These and other embodiments are disclosed herein. The preferred embodiments described herein do not limit the scope of this disclosure.

NOTATION AND NOMENCLATURE

Certain terms are used throughout the following description and claims to refer to particular system components. Persons skilled in the art will appreciate that components may be denoted in the art by different names. The present invention includes within its scope all components, however denoted in the art, that achieve the same function. In the following discussion and in the claims, the terms "including" and "comprising" are used in an open-ended fashion, and thus should be interpreted to mean "including, but not limited to." Also, the terms "couple," "couples" or "coupled" are intended to refer to either an indirect or direct connection. Thus, if a first device couples to a second device, that connection may be through a direct connection, or through an indirect connection via other devices and connections. The term "therapy" refers to a collection of one or more settings in an implantable medical device that dictate how the device operates to treat the patient.

BRIEF DESCRIPTION OF THE DRAWINGS

For a more detailed description of the preferred embodiments of the present invention, reference will now be made to the accompanying drawings, wherein.

DETAILED DESCRIPTION OF THE PREFERRED EMBODIMENTS

The present invention is susceptible to implementation in various embodiments. The disclosure of specific embodiments, including preferred embodiments, is not intended to limit the scope of the invention as claimed unless expressly specified. In addition, persons skilled in the art will understand that the invention has broad application. Accordingly, the discussion of particular embodiments is meant only to be exemplary, and does not imply that the scope of the disclosure, including the claims, is limited to specifically disclosed embodiments.

Figure 1:
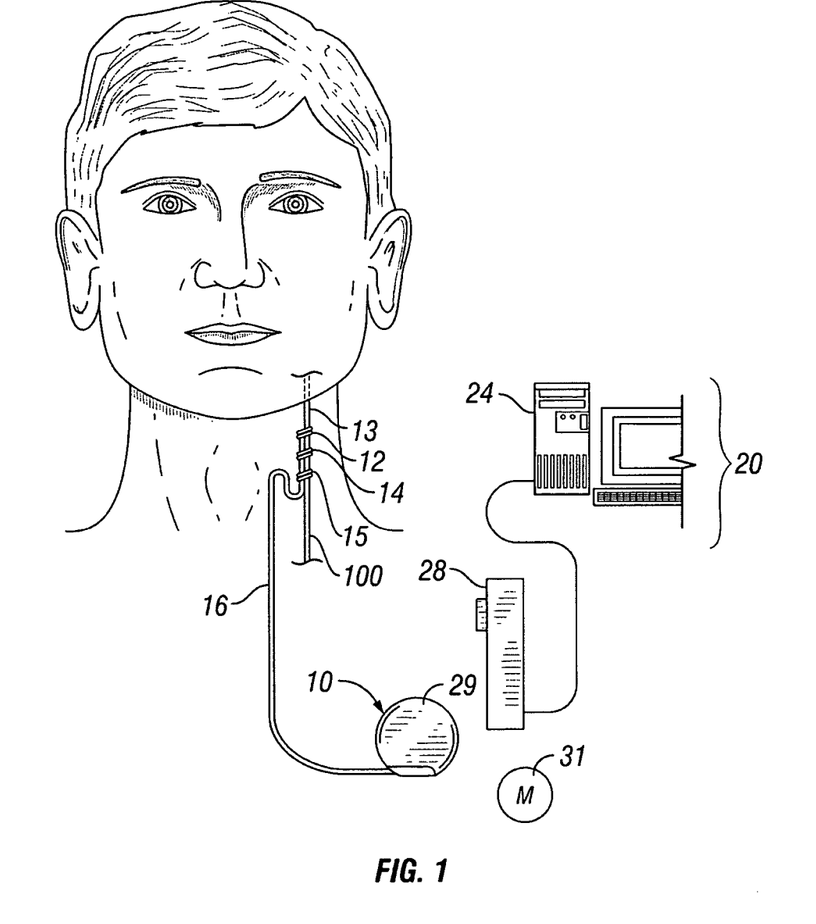
FIG. 1 depicts, in schematic form, an implantable medical device, in accordance with a preferred embodiment of the invention, implanted within a patient and programmable by an external programming system.

FIG. 1 illustrates an implantable medical device ("IMD") 10 implanted in a patient. The IMD 10 may be representative of any of a variety of medical devices. At least one preferred embodiment of the IMD 10 comprises a neurostimulator for applying an electrical signal to a neural structure in a patient, particularly a cranial nerve such as a vagus nerve 13. As used herein "stimulate" and "modulate" both refer to the delivery of such an electrical signal to a target body structure, regardless of whether the signal causes a particular effect such as an induction of an action potential in a stimulated nerve. Although the device 10 is described below in terms of vagus nerve stimulation ("VNS"), the disclosure and claims that follow are not limited to VNS, and may be applied to the delivery of an electrical signal to modulate the electrical activity of other cranial nerves such as the trigeminal and/or glossopharyngeal nerves, or to other neural tissue such as one or more brain structures of the patient, spinal nerves, and other spinal structures. Further still, the IMD 10 can be used to stimulate tissue other than nerves or neural tissue. An example of such other tissue comprises cardiac tissue.

Referring still to FIG. 1, a lead assembly comprising one or more leads 16 is coupled to the IMD 10 and includes one or more electrodes, such as electrodes 12 and 14. Each lead 16 has a proximal end that connects to the IMD 10 and a distal end on which one or more electrodes are provided. The outer housing (or "can") 29 of the IMD 10 preferably is electrically conductive and thus can also function as an electrode. The electrodes, such as electrodes 12, 14 and can 29, can be used to stimulate and/or sense the electrical activity of the associated tissue (e.g., the vagus nerve 13). An example of an electrode suitable for coupling to a vagus nerve to provide VNS therapy to a patient is disclosed in U.S. Pat. No. 4,979,511, incorporated herein by reference. Strain relief tether 15 comprises an attachment mechanism that attaches the lead assembly 16 to the vagus nerve to provide strain relief and is described in U.S. Pat. No. 4,979,511, incorporated herein by reference.

FIG. 1 also illustrates an external device implemented as a programming system 20 for the IMD 10. The programming system 20 comprises a processing unit coupled to a wand 28. The processing unit 24 may comprise a personal computer, personal digital assistant (PDA) device, or other suitable computing device consistent with the description contained herein. Methods and apparatus for communication between the IMD 10 and an external programming system 20 are known in the art. Representative techniques for such communication are disclosed in U.S. Pat. No. 5,304,206, and U.S. Pat. No. 5,235,980, both incorporated herein by reference. As explained below, the IMD 10 includes a transceiver (such as a coil) that permits signals to be communicated wirelessly and noninvasively between the external wand 28 and the implanted IMD 10. Via the wand 28, the programming system 20 generally monitors the performance of the IMD and downloads new programming information into the device to alter its operation as desired. Preferably, the IMD 10 also comprises a Reed switch that can be opened or closed by a magnet 31 that is placed in close proximity to the IMD. The transceiver and Reed switch internal to the IMD function as user input sense devices that sense external user input. As explained below, such user input sense devices can be used to control the IMD 10 as it sequences through a series of pre-programmed therapies. Sequencing through pre-programmed therapies means causing the IMD to provide each therapy one at a time in a prescribed order that is preset or programmable.

Figure 2:
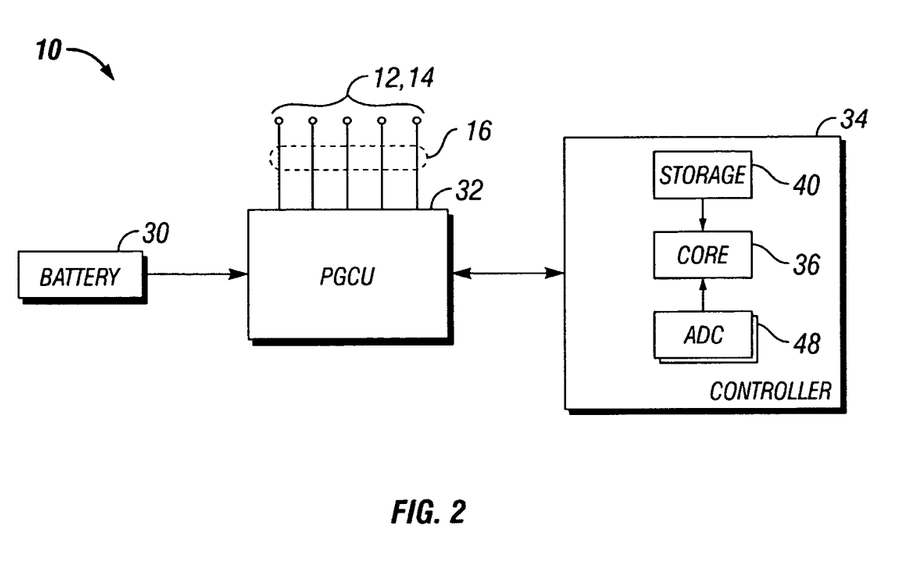
FIG. 2 is a block diagram of the implantable medical device of FIG. 1 and comprising a pulse generator and communication unit.

FIG. 2 shows a block diagram of one embodiment of the IMD 10. As shown, the IMD 10 includes a battery 30, a pulse generation and communication unit ("PGCU") 32, and a controller 34. Under the control of controller 34, the PGCU 32 may generate an electrical signal to stimulate a tissue in a patient. The battery 30 provides power for both the PGCU 32 and the controller 34. As explained in greater detail with respect to FIG. 3, the PGCU 32 includes a voltage regulator 58 that receives voltage from the battery 30 and provides operating voltage for use by the controller 34. In this way, the PGCU 32 can control the voltage provided to the controller 34. The controller 34 generally assists, controls, and/or programs the PGCU 32. Controller 34 preferably is, or includes a processor such as a low-power, mixed-signal microcontroller. In general, any suitable processor can be used to implement the functionality performed by the controller 34 as explained herein. It will be appreciated that some features of the controller 34 may also be provided in whole, or in part, by the PGCU 32, and vice versa. Thus, while certain features of the present invention may be described as comprising part of the PGCU 32, it is not intended thereby to preclude embodiments in which the features are provided by the controller. Likewise, certain features described herein as comprising part of the controller 34 are not intended to preclude embodiments in which the features comprise part of the PGCU 32.

The controller 34 preferably comprises an execution core 36 coupled to one or more analog-to-digital converters (ADCs) 48 and storage 40. The storage 40 preferably comprises volatile and/or non-volatile memory. The non-volatile memory may comprise Flash memory. The volatile memory may comprise any suitable type of random access memory (RAM). The storage 40 is used to store code that is executed by the core 36. Such executable code may be loaded into the IMD 10 during manufacturing and/or may be downloaded to the IMD from the programming system 20 after implantation. The executable code may be loaded into non-volatile memory and either executed directly from the non-volatile memory or copied to the volatile memory for execution therefrom.

The storage 40 may also be used to store the device settings that pertain to a therapy. In accordance with preferred embodiments of the invention, the IMD 10 may be programmed with a plurality of therapy programs. The therapy programs may be loaded into storage 40 during manufacturing and/or downloaded to the IMD 10 using programming system 20 after implantation. Each therapy program comprises one or more parameters including, for example, pulse width, current amplitude, frequency, on time, off time, and the like. The parameter settings determine the nature of the therapeutic electrical signal to be provided. Storage 40 therefore stores the parameter settings for each of multiple therapy programs. The controller 34 can cause the PGCU to operate in accordance with any of the therapy programs stored in storage 40 by, as explained below, programming the associated parameter settings into registers in the PGCU.

Figure 3:
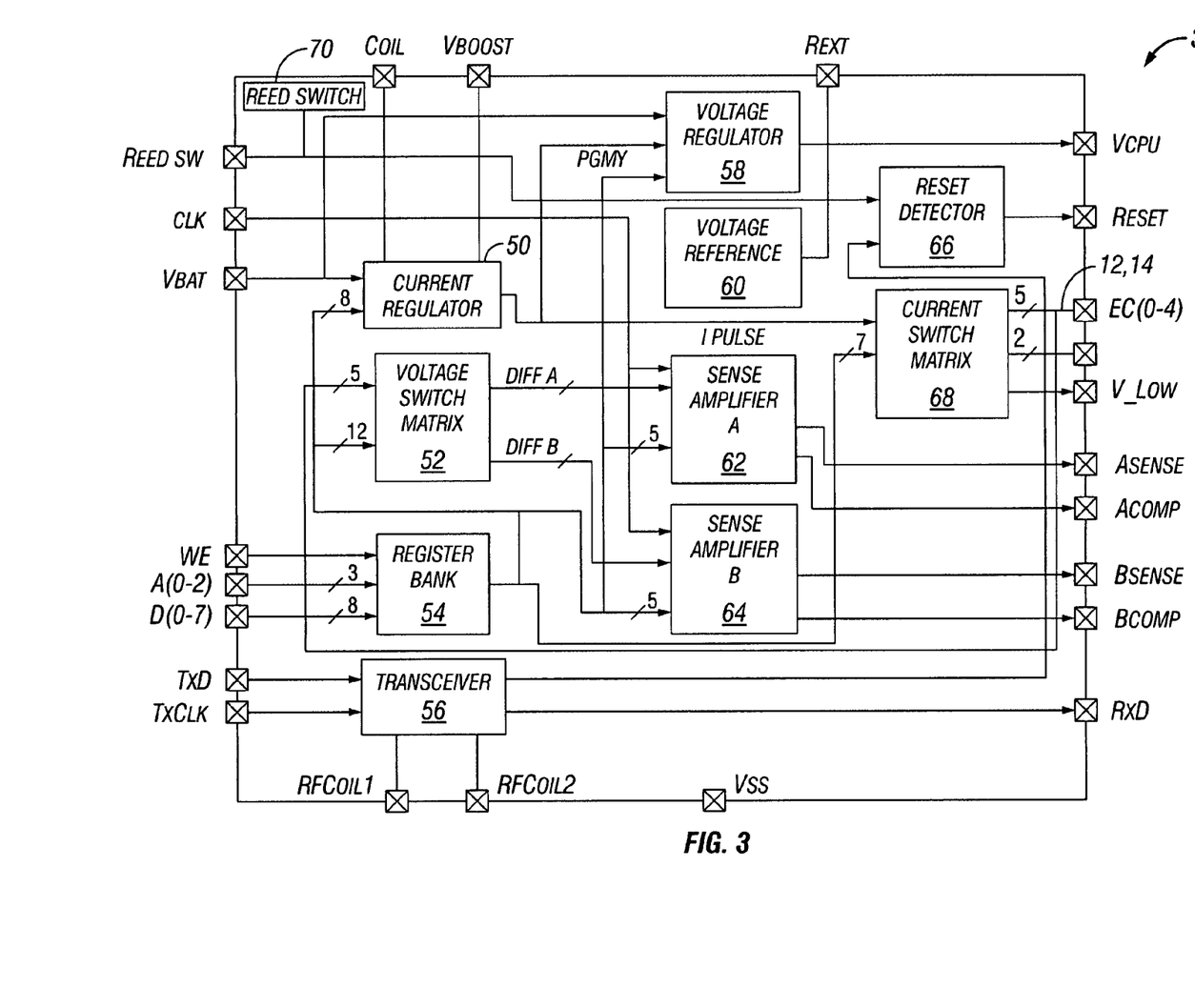
FIG. 3 is a block diagram of the pulse generator and communication unit of FIG. 2.

FIG. 3 is a block diagram showing a preferred embodiment of the PGCU 32 depicted in FIG. 2. Although a particular architecture for PGCU 32 is provided in FIG. 3 and discussed more fully hereafter, the recitation of a particular architecture is not intended to limit the scope of the invention, which is limited only by the claims. The PGCU 32 comprises a current regulator 50, a voltage switch matrix 52, a register bank 54, a transceiver 56, a voltage regulator 58 (previously noted), a voltage reference 60, a pair of sense amplifiers 62 and 64, a reset detector 66, and a current switch matrix 68. The aforementioned components preferably are coupled together on a single integrated circuit chip, but may also be implemented with other suitable architectures, including individual components or modules, although in general, integration of the components in a small number of modules increases reliability and reduces cost.

In accordance with the embodiment of FIG. 3, the register bank 54 comprises one more registers that can be written to and/or read by controller 34. The registers comprise registers used, at least in part, for programming the PGCU 32 to operate in accordance with a particular therapy program. As such, the registers in the register bank 54 are used to program such parameters as pulse width, frequency, current magnitude, on time, off time, and the like. Different, fewer or additional parameter settings can be programmed into the registers in other embodiments.

The voltage regulator 58 in the PGCU 32 receives voltage from the battery 30 and provides operational supply voltage for the controller 34. The voltage regulator 58 also provides a suitable voltage for the controller to reprogram its non-volatile flash memory in storage 40 if such memory is present in storage 40. The voltage level suitable for operating the controller may differ from, or be the same as, the voltage level suitable for reprogramming the non-volatile flash memory and the voltage regulator 58 provides both voltage levels to the controller.

The transceiver 56 generally permits the external programming system 20 via wand 28 to communicate with the IMD 10. Transceiver 56 permits the external programming system 20 to program the IMD 10 with, for example, parameter settings pertaining to one or more therapy programs, to monitor the configuration and state of the IMD, and to download executable code into the IMD 10. In addition, transceiver 56 also permits the external programming system 20 to inform the implanted IMD 10 of the occurrence of a physiological event such as a seizure.

A Reed switch 70 may also be included in or connected to the PGCU 32. A Reed switch is a switch that opens or closes depending on a magnetic field. For example, a normally-open Reed switch can be made to close by placing an external magnet (e.g., magnet 31 in FIG. 1) in close proximity to the site on the body at which the IMD is implanted. Similarly, a normally-closed Reed switch can be made to open via a closely located magnet. The Reed switch can be used in two ways. First, a user placing magnet 31 close to the IMD 10 in combination with sustained signals from transceiver 56 can cause the IMD to be reset. The Reed Switch 70 is coupled to reset detector 66, or included within the reset detector logic, and causes the reset detector to generate a Reset signal to the controller 34 when in combination with sustained signals from transceiver 56. Second, and as explained below in greater detail, the Reed switch 70 can be used to permit a patient control over the operation of the IMD as it sequences through a series of therapy programs.

The current regulator 50 delivers an electrical current signal determined by the controller 34 to the patient via lead 16 and stimulating electrodes 12, 14. The IMD 10 preferably provides a constant current, used herein to refer to providing a predetermined current or pulse shape that is independent of the impedance across the leads (i.e., the impedance presented by the patient's tissues). To overcome this impedance, the current regulator 50 increases the battery voltage to a voltage that is determined by a value programmed into the register bank 54, while maintaining the current at a controlled magnitude. The magnitude of the current delivered to the patient also is programmable by programming system 20 and controller 34 by writing a desired value into the register bank 54.

The current switch matrix 68 preferably provides current from current regulator 50 to any desired electrode or sensor from among those provided in IMD 10 as programmed by the controller 34. Such electrode and sensor inputs are labeled as EC(0-4) and comprise at least electrodes 12, 14. Where electrodes are used as the sensing elements, a voltage signal from the selected electrodes is provided for conversion from analog to digital form by the controller 34 (which preferably has one or more internal analog-to-digital converters 48, FIG. 2). The sense amplifiers 62 and 64 are used to detect electrophysiologic signals preferably in any desired frequency range such as from 1 to 100 Hz. The voltage switch matrix 52 connects the sense amplifiers 62 and 64 to any two or more selectable electrodes/sensors. The controller 34 can program registers in the register bank 54 to specify the particular electrodes or sensors that are selected to be coupled to each sense amplifier.

Figure 4:
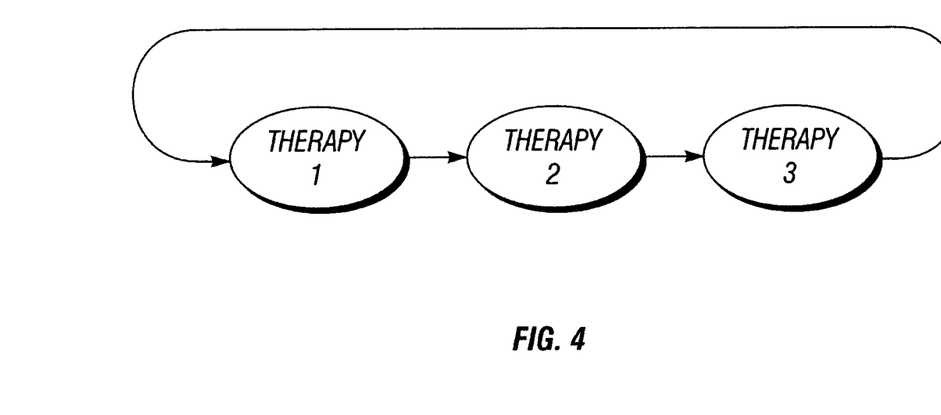
FIG. 4 illustrates sequencing from one therapy to another and repeating the sequence.

As explained previously, the IMD 10 can be programmed with multiple sets of therapy programs (referred to as "therapies"). The multiple programmed therapies can be used in a variety of ways. FIG. 4, for example, illustrates the use of three therapies, although the invention is not so limited and any number of therapy programs can be used. As shown, the three therapies comprise Therapy 1, Therapy 2, and Therapy 3. Each therapy is provided by the IMD for a particular period of time, known as the therapy program time, for the particular therapy. The therapy program time can be fixed or in some embodiments may be programmable, and may be the same or different for each of the various therapies. Where the amount of time the respective therapy programs will be used is programmable, the therapy program time may be included as an additional programmable parameter setting for each therapy program.

Providing a particular therapy from a programmed therapy sequence in the particular embodiments described herein comprises the controller 34 loading that therapy program's parameter settings (e.g., pulse width, amplitude, etc.) from storage 40 into the register bank 54 in the PGCU 32. In other embodiments, all of the therapies are loaded into registers or memory in the PGCU. The controller 34 loads the parameter settings for each therapy in turn into the register bank 54 thereby causing the IMD 10 to sequence through the multiple therapies, Therapies 1-3, and then back to Therapy 1. In the example of FIG. 4, the controller 34 programs Therapy 1 into the PGCU 32 to be provided for a first therapy program time. The controller 34 then programs the PGCU for Therapy 2 for a second therapy program time and then Therapy 3 for a third therapy program time, after which Therapy 1 is again programmed. The parameter settings for each subsequent therapy overwrites the previous therapy's parameter settings. The sequence automatically repeats at least once. In another embodiment, the number of sequence repeats may be programmed. In an alternative embodiment the total time for the IMD to cycle among the programmed therapies may be programmable as a total therapy sequence time parameter. Accordingly, the controller 34 may causes the PGCU 32 to cyclically implement a series of therapy programs with a great deal of flexibility available in implementing how the programs are to be performed. Using programmer 20, the order of the therapies in the sequence and the particular therapies selected to comprise the sequence can be programmed.

In some embodiments, IMD 10 automatically sequences from one therapy to another according to the fixed or programmed therapy program times for each therapy, and/or the total therapy sequence time. In other embodiments, the IMD 10 permits user intervention to cause the IMD to change from one therapy to the next by a manual signal. For example, the user may cause the IMD 10 to sequence from one therapy to the next by placing a magnet 31 in sufficient proximity to the IMD to trigger a Reed switch 70 that in turn causes the controller 34 to program the settings for the next scheduled therapy. The use of the magnet 31 is such that the IMD can differentiate a user desiring for the IMD 10 to sequence to the next therapy as opposed to the user desiring to reset the IMD. In this embodiment, the controller 34 is programmed as to the order of the therapies but requires the user to dictate when one therapy is to cease and the next therapy is to begin. In still other embodiments, a user can manually cause a change in therapies, but the controller 34 automatically switches from one therapy to the next if no user input has been received for a particular period of time (e.g., a preprogrammed time period).

In yet another embodiment, the controller 34 automatically sequences the IMD 10 cyclically through the therapies, but a person (e.g., the patient in which the IMD is implanted) can cause the controller to interrupt the sequencing process and remain operating in accordance with one particular therapy. The user triggers an input sense device (e.g., transceiver 56 or Reed switch 70) at a certain point within the cyclical therapy operation. In one variation on this embodiment, the IMD 10 continues operating in accordance with the therapy that was programmed into the PGCU 32 at the time that the user triggered the input sense device. For example, if the IMD is operating in accordance with Therapy 2 when the user positions a magnet 31 near the IMD 10, the IMD 10 continues operating in accordance with Therapy 2 and does not sequence to the next pre-programmed therapy, which is Therapy 3 in this example. In this way, if the user is satisfied with a particular therapy, the user can cause the IMD to remain operating with that particular therapy.

In another variation, when the user triggers the user input sense device, the IMD 10 interrupts the sequencing, and switches back to the preceding therapy. For example, if the IMD is operating in accordance with Therapy 2 when the user positions a magnet 31 near the IMD 10, the IMD 10 ceases operating in accordance with Therapy 2 and reverts back to Therapy 1. In this way, if the user was satisfied with an immediately preceding therapy, but not the current therapy, the user can cause the IMD to switch back to the previous satisfactory therapy. The use of the magnet is such as to inform the IMD 10 of whether the user desired the IMD to operate in accordance with the present therapy or the previous therapy.

In one example of the aforementioned embodiments, the various therapies in the sequence may differ in the current magnitude. That is, the current magnitude can be set to a therapeutically relatively low value for Therapy 1 and each subsequent therapy (Therapies 2 and 3) implements an increasingly higher current magnitude than the preceding therapy. The user can then determine his or her tolerance for the current magnitude and signal the IMD 10, for example, via programmer 20 or magnet 31, as to the therapy that has the preferred current magnitude for that particular patient. By triggering an interrupt and causing the therapy to either remain in the current therapy or revert to a prior therapy, the patient may be provided with a level of control of an otherwise automatic current ramping process.

In another variation of FIG. 4, the sequence of therapies does not repeat. Instead, the various therapies are implemented, one at a time, as described above, and the user can signal the IMD 10 (via magnet 31 or programmer 20) which therapy in the sequence is preferred. If, upon completing the sequence of therapies, the user has provided any such indication to the IMD 10, the IMD can either repeat the sequence as illustrated in FIG. 4 or transition to, and remain operating in accordance with, a predetermined therapy (e.g., Therapy 1).

Figure 5:
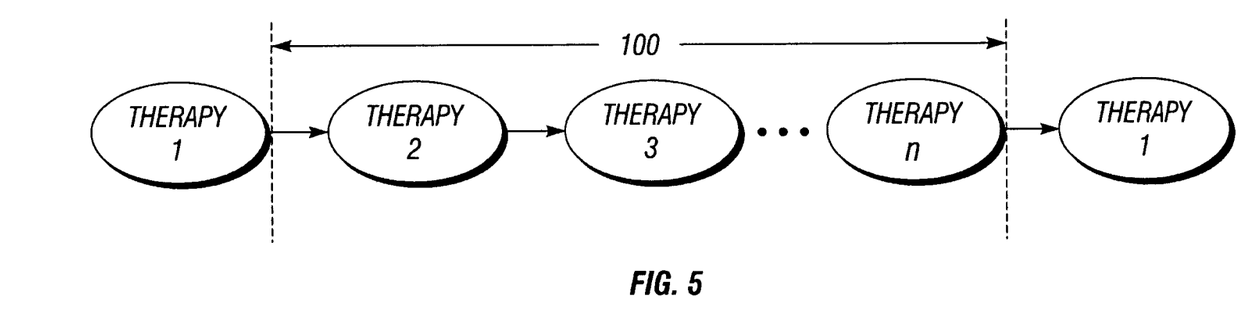
FIG. 5 illustrates interrupting a first therapy with a sequence of therapies and then re-implementing the first therapy.

FIG. 5 shows another embodiment in which a first therapy (Therapy 1) is implemented in the IMD 10 to provide a desired therapy for the patient. As noted above, it may be desired to conduct a medical procedure on the patient, for example to image the patient's brain, or other tissue, while the IMD 10 is operating in accordance with multiple sequential therapies. The IMD 10 of the preferred embodiment permits the programmer 20 to be used to cause the IMD to transition to a sequential mode of operation 100. While in sequential mode 100, the IMD 10 sequences through a plurality of therapies, for example, from Therapy 2 to Therapy 3, and so on, according to a fixed or programmed therapy program time for each therapy, and/or a total therapy sequence time. If desired, at least one of the therapies in sequential mode 100 may comprise Therapy 1. The IMD 10 may then transition back to Therapy 1, the therapy in place before sequential mode 100 began. Using programmer 20, the therapies included in mode 100 and the order of the therapies within mode 100 can be programmed. In the embodiment of FIG. 5, the sequence of therapies preferably is not automatically repeated, as is the case for the example of FIG. 4.

An exemplary use of the embodiment of FIG. 5 is as follows. While in mode 100, the patient's brain, or other tissue, can be imaged or another assessment of the patient can be made with the IMD 10 sequentially providing the programmed therapies for fixed or programmed therapy program times. The therapy program time for each therapy in sequential mode 100 may be the same or different for each therapy. The IMD 10 eventually transitions back to the prior operating therapy (Therapy 1 in the example of FIG. 5). Additionally or alternatively, the user (for example, a treating physician) can manually signal the IMD 10 (via magnet 31 or programmer 20) to move from one therapy to the next in the programmed therapy sequence and for the programmed therapy program times.

In the preceding embodiments pertaining to FIGS. 4 and 5, it may be desired to impose a time pause between sequential pairs of therapies. That time pause may be fixed or programmable. In some embodiments, the off time of a preceding therapy may comprise the time pause between that therapy and the next therapy in the therapy sequence.

Whether the IMD 10 operates in accordance with the embodiment of FIG. 4 in which the IMD continuously repeats a sequence of therapies, or in accordance with the embodiment of FIG. 5 in which the IMD ceases operating in accordance with a first therapy, sequences through a plurality of therapies, and then switches back to the previous therapy without repeating, the sequence may be programmed into the IMD 10 via programmer 20.

While the preferred embodiments of the present invention have been shown and described, modifications thereof can be made by persons skilled in the art without departing from the spirit and teachings of the invention. The embodiments described herein are exemplary only, and are not intended to limit the scope of protection provided herein.

What is claimed is:

1. A method of operating an implantable medical device (IMD) to provide neurostimulation, the method comprising:
    operating a first therapy program from a therapy sequence for a first therapy time, wherein a plurality of neurostimulation therapy programs comprising the therapy sequence are stored in the IMD before any of the neurostimulation therapy programs are operated;
    the IMD automatically operating a second therapy from the therapy sequence in the IMD for a second therapy time following the first therapy time; and
    the IMD automatically repeating the therapy programs in the therapy sequence.

2. The method of claim 1 wherein the first therapy time and the second therapy time are substantially the same.

3. The method of claim 1 wherein the first therapy time and the second therapy time are different.

4. The method of claim 1 wherein the first and second therapy times are determined by an elapsed time, an indication from outside the IMD, or combination thereof.

5. The method of claim 1 wherein the plurality of neurostimulation therapy programs are stored by programming a plurality of parameters to define each neurostimulation therapy program in the therapy sequence, and wherein the plurality of parameters comprises at least two parameters selected from a current amplitude, a pulse width, a frequency, an on time, an off time, a therapy program time, a total therapy sequence time, or combinations thereof.

6. The method of claim 1 wherein the first therapy program is operated automatically by the IMD.

7. The method of claim 1 further comprising:
the IMD receiving a wireless signal from an external system, the wireless signal instructing the IMD to continue operating a particular therapy program that is operating when the signal is received, and to discontinue automatically repeating the therapy programs in the therapy sequence.

8. The method of claim 1 further comprising:
the IMD receiving a wireless signal from an external system, the wireless signal instructing the IMD to discontinue automatically repeating the therapy programs in the therapy sequence, and to begin operating a first particular therapy program that was operating immediately preceding a second particular therapy program that was operating when the signal was received.

9. The method of claim 1 further comprising:
(d) operating a third therapy program from the therapy sequence in the IMD for a third therapy time following the second therapy time.

10. A method, comprising:
operating a first therapy program in an implantable neurostimulator, wherein the implantable neurostimulator stores the first therapy program and a plurality of additional therapy programs;
automatically causing the implantable neurostimulator to sequence through the plurality of additional therapy programs in a therapy sequence; and
after the therapy sequence, automatically operating and continuing the first therapy program in the neurostimulator and not automatically repeating automatically causing the implantable neurostimulator to sequence through the plurality of additional therapy programs in the therapy sequence.

11. The method of claim 10 wherein the therapy sequence comprises the first therapy program.

12. The method of claim 10 wherein the first therapy program and each of the plurality of additional therapy programs comprise a plurality of parameters selected from a current amplitude, a pulse width, a frequency, an on time, an off time, a therapy program time, a total therapy sequence time, or combinations thereof.

13. An implantable medical device (IMD), comprising:
an electrical signal generator configured to provide an electrical signal to stimulate a neural structure of a patient;
a controller coupled to the electrical signal generator, the controller configured to cause a plurality of therapy programs to be operated by the electrical signal generator in an automatic, cyclically-repeated sequence; and
wherein the plurality of therapy programs are stored in the IMD before the automatic, cyclically-repeated sequence begins.

14. The implantable medical device of claim 13 wherein the controller automatically sequences through the plurality of therapy programs, each therapy program being operated for a therapy sequence time.

15. The implantable medical device of claim 14 wherein the therapy sequence time is the same for each therapy program.

16. The implantable medical device of claim 13 further comprising a user-input sense device and wherein the controller sequences from one therapy program to a next therapy program when indicated by a user input.

17. The implantable medical device of claim 13 wherein the controller implements each of the plurality of therapy programs for an amount of time that is a programmed time for each therapy.

18. The implantable medical device of claim 13 wherein each of the plurality of therapy programs comprises a plurality of parameters selected a current amplitude, a pulse width, a frequency, an on time, an off time, a therapy program time, a total therapy sequence time, or combinations thereof.

19. An implantable medical device, comprising:
an electrical signal generator configured to provide an electrical signal to stimulate a neural structure of a patient;
a controller coupled to the electrical signal generator, the controller configured to automatically cause a first therapy program operated by the electrical signal generator to be interrupted, a plurality of therapy programs to subsequently be implemented in programmed sequence automatically by the electrical signal generator, and the first therapy program to again be operated automatically; and
storage internal to the implantable medical device in which the first therapy program and the plurality of therapy programs are pre-stored.

20. The implantable medical device of claim 19 wherein the controller automatically sequences through the plurality of therapy programs.

21. The method of claim 1 further comprising:
interrupting the repeating of the therapy programs; and
operating a particular therapy program selected from the therapy sequence.

22. The method of claim 21 wherein the particular therapy program is selected from a current therapy program in the therapy sequence, wherein the current therapy program is the therapy program operating when repeating of the therapy programs is interrupted;
a previous therapy program operating immediately prior to the current therapy program;
and a last therapy program in the therapy sequence.

23. The method of claim 21 wherein subsequent therapy programs in the therapy sequence operate with a greater current magnitude than an immediately preceding therapy program.

* * * * *